United States Patent [19]

Okabe et al.

[11] 4,426,390

[45] Jan. 17, 1984

[54] NOVEL β-LACTAM COMPOUNDS, PROCESS FOR PRODUCING THEREOF, AND USE THEREOF AS MEDICINES

[75] Inventors: Mitsuyasu Okabe, Fujisawa; Takeo Yoshioka, Ayase; Yasuo Fukagawa, Kamakura; Rokuro Okamoto, Fujisawa; Kageaki Kouno, Tokyo; Tomoyuki Ishikura, Chigasaki, all of Japan

[73] Assignee: Sanraku-Ocean Co., Ltd., Tokyo, Japan

[21] Appl. No.: 306,931

[22] Filed: Sep. 29, 1981

[30] Foreign Application Priority Data

Oct. 1, 1980 [JP] Japan .................. 55-135829
Oct. 17, 1980 [JP] Japan .................. 55-144507
Dec. 5, 1980 [JP] Japan .................. 55-170864

[51] Int. Cl.³ .................. C07D 487/04; A61K 31/40
[52] U.S. Cl. .................. 424/274; 260/245.2 T; 424/114; 435/119
[58] Field of Search .................. 260/245.2 T; 424/274

[56] References Cited

U.S. PATENT DOCUMENTS 3,950,357 4/1976 Kahan et al. .................. 260/245.2 T

OTHER PUBLICATIONS

Journal of Antibiotics, vol. 32, pp. 1-12 (1979).

Primary Examiner—Mary C. Lee
Attorney, Agent, or Firm—Wenderoth, Lind & Ponack

[57] ABSTRACT

A compound of the formula

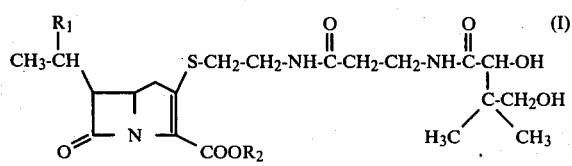

wherein $R_1$ represents a hydrogen atom, —OH or —O-$SO_3H$, and $R_2$ represents a hydrogen atom or an unsubstituted or substituted benzyl group; and a salt thereof; processes for production thereof by fermentation; and uses thereof as antimicrobial agents.

7 Claims, No Drawings

NOVEL β-LACTAM COMPOUNDS, PROCESS FOR PRODUCING THEREOF, AND USE THEREOF AS MEDICINES

This invention relates to novel β-lactam compounds, and more specifically, to carbapenem compounds of the following general formula

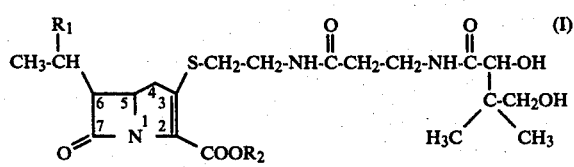

wherein $R_1$ represents a hydrogen atom, —OH, or —OSO$_3$H, and $R_2$ represents a hydrogen atom or an unsubstituted or substituted benzyl group, and salts thereof, processes for production thereof, and uses thereof as antimicrobial agents.

Antibiotics having a 7-oxo-1-azabicyclo[3.2.0]-hept-2-ene-2-carboxylic acid skeleton of the formula

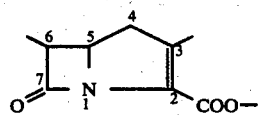

generally have high antimicrobial activity and β-lactamase inhibitory activity. Various 7-oxo-1-azabicyclo[3.2.0]hept-2-ene-2-carboxylic acid derivatives or carbapenem compounds have heretofore been produced by fermentative, semi-synthetic and wholly synthetic methods. These antibiotic substances include, for example, thienamycin disclosed in Journal of Antibiotics, Vol. 32 (1979), pages 1 to 12; epithienamycins disclosed in Abstracts 80 and 81 of the 17th Interscience Conference on Antimicrobial Agents and Chemotherapy (1977); N-acetylthienamycin disclosed in West German Pat. No. 2652681 (1977); olivanates disclosed in Journal of Antibiotics, Vol. 32 (1979), pages 287 to 304; PS-5 disclosed in Journal of Antibiotics, Vol. 32 (1979), pages 262 to 286; PS-6 disclosed in Japanese Laid-Open Patent Publication No. 59295/1979; and PS-7 disclosed in Japanese Laid-Open Patent Publication No. 92983/1979.

The compounds of formula (I) provided by this invention are novel carbapenem antibiotics not described in the prior literature, and are structurally characterized by the fact that they have a pantetheinyl group at the 3-position and an ethyl group optionally substituted by —OH or —OSO$_3$H at the 6-position in the 7-oxo-1-azabicyclo[3.2.0]hept-2-ene-2-carboxylic acid skeleton. The present inventors have termed a series of these carbapenem antibiotics "antibiotic OA-6129A" [a compound of formula (I) in which $R_1$ and $R_2$ are H], "antibiotic OA-6129B" (a compound of formula (I) in which $R_1$ is —OH and $R_2$ is H], and "antibiotic OA-6129C" (a compound of formula (I) in which $R_1$ is —OSO$_3$H and $R_2$ is H). In the present specification, these antibiotics are generically referred to as "antibiotic OA-6129".

The antibiotics of formula (I) are unique in that they are more stable than the previously described carbapenem antibiotics having the same basic skeleton. In addition, compounds of formula (I) in which $R_2$ represents a hydrogen atom, and their salts are useful as antimicrobial agents because, similar to the carbapenem compounds described in the above-cited references, they have strong antimicrobial activity and β-lactamase inhibitory activity and also possess the ability to synergetically potentiate the anti-microbial activity of conventional penicillins and cephalosporins against β-lactamase producing microorganisms.

In the substituted benzyl group represented by $R_2$ in the above formula (I), the substituent on the benzene ring includes, for example, lower alkyl groups such as methyl and ethyl, lower alkoxy groups such as methoxy and ethoxy, halogen atoms such as chlorine and fluorine, and a nitro group. The benzene ring may be substituted by 1 to 3 such substituent groups. Examples of the substituted benzyl groups are p-nitrobenzyl, p-bromobenzyl, p-methylbenzyl, 2,4-dinitrobenzyl, and p-methoxybenzyl groups. Benzyl and p-nitrobenzyl groups are preferred as the unsubstituted or substituted benzyl group represented by $R_2$.

The carboxyl group at the 2-position of compounds of formula (I) in which $R_2$ is a hydrogen atom may be in the form of salts. Examples of such salts include alkali metal salts such as sodium, potassium and lithium salts, alkaline earth metal salts such as calcium and magnesium salts, other metal salts such as aluminum salts, ammonium salt, primary, secondary or tertiary amine salts such as monoethylamine, dimethylamine, trimethylamine, monoethanolamine and diethanolamine salts, and salts of organic bases such as benzathine and procaine salts. Of these, pharmaceutically acceptable salts are preferred, and the alkali metal salts such as sodium and potassium salts are especially preferred.

According to the invention, compounds of general formula (I) in which $R_2$ is a hydrogen atom, that is antibiotics OA-6129 of the following formula

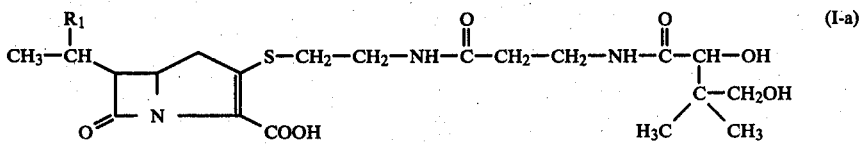

wherein $R_1$ is as defined above, can be produced by a method which comprises cultivating a microorganism having the ability to produce antibiotic OA-6129 of formula (I-a) having β-lactamase inhibitory activity in a nutrient medium, and recovering antibiotic OA-6129 from the culture broth.

The antibiotic OA-6129-producing microorganism used in this invention may be selected from various genera of microorganisms, which have the ability to produce the antibiotic OA-6129 of formula (I-a) having the physicochemical and biological properties described hereinbelow.

Microorganisms suitable for the object of this invention can be screened out in the following manner. Using the principle of the below-described screening technique, everyone skilled in the art can easily obtain an antibiotic OA-6129-producing microorganism which can be used in this invention.

Specifically, filtrates of culture broths of soil isolates are bio-assayed on an agar plate of a β-lactam-susceptible detector organism and on agar plates of the detector containing various types of β-lactamase so that candidate microorganisms which give significant inhibitory zones on the first-mentioned agar plate but smaller inhibitory zones on at least some of the latter β-lactamase agar plates. The active components in the culture broths of the selected organisms are adsorbed on active carbon, and the eluates are analysed by paper chromatography or thin-layer chromatography. If antibiotic OA-6129 is detected therefrom by bioautography using a β-lactam-susceptible detector organism, such soil isolates can be determined to be antibiotic OA-6129-producers which are useful in the process of this invention.

This screening method is described more specifically below.

A Comamonas assay plate to be described hereinbelow is used as the β-lactam-hypersensitive bioassay agar plate. For efficient detection of β-lactam, β-lactamases from *Bacillus cereus* 569 and *Citrobacter freundii* E-9 are added to the Comamonas assay plate, giving the three types of bioassay agar plates in total (Comamonas assay plate; Comamonas CV assay plate with *Bacillus cereus* 569 β-lactamase; Comamonas CM assay plate with *Citrobacter freundii* E-9 β-lactamase). Filtrates of culture broths of soil isolates are impregnated in 8 mm pulp discs, and placed on the three assay plates respectively. After incubation at 35° C. for 20 hours, those soil isolates are selected which give significant inhibitory zones on the Comamonas assay plate but smaller inhibitory zones on at least one of the Comamonas CV and Comamonas CM assay plates.

To the culture broth filtrates of the selected microbes is added activated carbon ("Shirasagi" active carbon, a special product of Takeda Chemical Co., Ltd.) in an amount of 2% (W/V) of the filtrate. The suspensions are stirred for 15 minutes, and centrifuged. The precipitates are collected and washed with the same volumes of distilled water as the broth filtrates. After centrifugation, the precipitates are mixed with the half volumes of the culture broth filtrates of 50% (W/V) acetone. The suspensions are stirred at room temperature for 30 minutes, and centrifuged to provide supernatant solutions. The supernatants are concentrated about 20 times at 30° to 35° C. in a rotary evaporator. The concentrates are spotted on a sheet of filter paper Toyo No. 50 (a product of Toyo Roshi Kaisha, Ltd.) and subjected for 16 hours to descending paper chromatography using a solvent mixture of 80% acetonitrile/Tris/EDTA [consisting of 120 ml of acetonitrile, 30 ml of 1/10 M tris(hydroxymethyl) aminomethane hydrochloride buffer having a pH of 7.5, and 1 ml of 0.1 M sodium ethylenediaminetetraacetate, pH 7.5] followed by bioautography using *Comamonas terrigena* B-996 as an aasay organism. Soil isolates which show inhibitory zones at a migration distance (Rf value) corresponding to antibiotic OA-6129 A, B or C are selected as candidates having the ability to produce antibiotic OA-6129.

The selected candidates are further determined for their production of antibiotic OA-6129 by paper chromatography and thin-layer chromatography.

By the above procedure, everyone skilled in the art can easily screen out antibiotic OA-6129-producing microorganisms which can be used in this invention.

Typical examples of antibiotic OA-6129-producing microorganisms screened in the above manner include those belonging to the genus Streptomyces. One suitable example is a strain of the genus Streptomyces which was isolated from the soil sample collected near Sumiyoshi Shrine, Fukuoka-shi, Fukuoka-ken, Japan and numbered strain OA-6129 by the present inventors.

The OA-6129 strain has the following microbiological properties.

(1) Morphology

On slide glass cultivation, straight to flexuous aerial mycelia without verticillate branches are observed from the well-branched substrate mycelia. The mature spore chain consists of at least 10 elliptical to cylindrical spores, and no sporangium is noted. Spores are about $0.6-1.0\times0.7-2.5$ microns in size and have smooth surfaces. No flagellated spore is observed.

(2) Growth in various culture media

Cultivation is carried out at 28° to 30° C. unless specifically indicated. The colors are described mainly in accordance with the method described by H. D. Tresner and E. J. Backus (Journal of Applied Microbiology, Vol. 11, No. 4, pages 335 to 338 (1963)), and the symbols shown in the parentheses [ ] (CHM code) are those given in Color Harmony Manual of Container Corporation of America.

(1) Sucrose-nitrate agar

Yellowish gray [2dc] to grayish yellow pink [5dc] aerial mycelia occur on a moderate growth tinted with yellowish gray [2dc] to light grayish yellow brown [3ge]. No soluble pigment is formed.

(2) Glucose-asparagine agar

Light gray [d] aerial mycelia are observed on an abundant growth tinted with pale yellow [2db] to light olive brown [2ge], later turning to be grayish yellow pink [5dc]. No soluble pigment is observed.

(3) Glycerol-asparagine agar (ISP-5 medium)

Light gray [d] to light grayish redish brown [5fe] aerial mycelia occur on a good growth tinted with moderately yellowish pink [4gc] to light brown [4ie]. No soluble pigment is produced.

(4) Starch-inorganic salt agar (ISP-4 medium)

Light gray [d] aerial mycelia are formed on a good growth colored with pale yellow [2db] to gray [2fe]. No soluble pigment is noted.

(5) Tyrosine agar (ISP-7 medium)

Light gray [d] to light brownish gray [3fe] aerial mycelia on a grayish yellow [3ec] to light brown [4ie] growth are observed with slightly brownish pigmentation in the medium.

(6) Nutrient agar

Light grayish reddish brown [5fe] aerial mycelia occur on an abundant growth tinted with pale yellow [2db] or light yellow [2fb] to light olive brown [2ge]. No soluble pigment is noted.

(7) Yeast extract-malt extract agar (ISP-2 medium)

Grayish yellow pink [5dc], or at a somewhat later stage light gray [d], aerial mycelia on an abundant growth colored with moderately yellowish pink [4gc] to light brown [4ie] are observed without soluble pigment.

(8) Oatmeal agar (ISP-3 medium)

Light brownish gray [3fe] to light grayish reddish brown [5fe] aerial mycelia occur on a good growth tinted with grayish yellow [3ec] to light orange yellow [3ea]. The medium colors slightly brown around colonies.

(9) Calcium malate agar

Light gray [d] to light grayish reddish brown [5fe] aerial mycelia are noted on a moderate growth colored with dark to yellowish gray [2dc] without soluble pigment. The calcium salt dissolves around mature colonies.

(10) Glucose-peptone-gelatin (cultivated at 20° C.)

White [b] to grayish yellow pink [5cb] aerial mycelia occur on a good growth tinted with pale yellow [2db] to brown. When the cultivation period is prolonged (for more than about 3 weeks), a brown soluble pigment forms.

(3) Physiological properties (1) Growth temperature

The strain was cultivated on yeast extract-malt extract agar (ISP-2 medium) at temperatures of 10°, 20°, 25°, 30°, 34°, 37°, 40°, 45° and 50° C., respectively. It can scarcely grow at 37° C., and not at all above 40° C. Although it grows at the other temperatures, the optimal growth temperature appears to be in the range of 20° to 30° C.

(2) Liquefaction of gelatin: positive (3) Hydrolysis of starch: positive (4) Coagulation and peptonization of skimmed milk: Peptonized without coagulation (5) Formation of a melanoid pigment:

No melanoid pigment is formed in peptone-yeast extract-iron agar (ISP-6 medium) and tryptone-yeast extract broth (ISP-11 medium). In tyrosine agar, very slightly brown color is observed with a trace amount of melamin.

(4) Utilization of various carbon sources (in Pridham and Gottlieb agar)

(1) L-arabinose: +
(2) D-xylose: +
(3) D-glucose: +
(4) D-fructose: +
(5) sucrose: questionable
(6) inositol: −
(7) L-rhamnose: +
(8) raffinose: −
(9) D-mannitol: +

+: utilized; −: not utilized

From the above microbiological properties, it is concluded that the OA-6129 strain is a streptomycete belonging to Section Rectiflexibiles. The surface of spores is smooth. The color of aerial mycelia is light gray [d] on most culture media such as oatmeal agar, glycerol-asparagine agar and starch-inorganic salt-agar, indicating the gray series. But this strain sometimes produces grayish yellow pink [5dc] mycelia, on sucrose-nitrate agar, yeast extract-malt extract agar and glucose-asparagine agar depending upon the phase of cultivation, suggesting the red series. The color of substrate mycelia is pale yellow to grayish yellow at an early stage of cultivation in all the tested culture media, later becoming yellowish brown to grayish yellow brown or brown. No formation of a melanoid pigment is observed in peptone-yeast extract-iron agar and tryptone-yeast extract broth. Other water-soluble pigments are not formed in most media, either a slightly brown pigment is noted in tyrosine agar, glucose-peptone-gelatin and oatmeal agar.

The present inventors deposited this strain as Streptomyces sp. OA-6129 at Fermentation Research Institute, Agency of Industrial Science and Technology, Japan, 1-3, Higashi 1-chome, Yatabe-machi, Tsukuba-gun, Ibaraki-ken, Japan under the Badapest Treaty on the International Recognition of the Deposit of Microorganisms for the Purposes of Patent Procedure. Deposit Number FERM BP-11 has been assigned to this strain.

The antibiotic OA-6129 of formula (I-a) can be produced by inoculating an antibiotic OA-6129-producing microorganism, for example, spores or mycelia of Streptomyces sp. OA-6129, in a nutrient medium, and aerobically cultivating it.

Nutrient sources employed in this invention may be assimilable ones commonly used for cultivation of actinomycetes, such as carbohydrates, nitrogen sources and inorganic salts. They include, for example, carbohydrates such as glucose, glycerol, maltose, sucrose, molasses, dextrin and starch; oils and fats such as soybean oil, peanut oil and lard; nitrogen sources such as peptone, meat extract, soybean meal, cotton seal meal, dried yeast, corn steep liquor, yeast extract, skimmed milk, casein, sodium nitrate, ammonium nitrate and ammonium sulfate; and inorganic salts such as dipotassium phosphate, sodium chloride, calcium carbonate and magnesium sulfate. If required, traces of metals such as cobalt and manganese may be added to the culture medium. Other nutrient sources may also be used which can support the growth of antibiotic OA-6129-producing organisms, leading to the substantial production of antibiotic OA-6129. Accordingly all nutritional materials for known actinomycetes can be used without difficulty. An antifoamer such as silicone and vegetable oils may be added to inhibit foaming during autoclaving and cultivation.

The mixing proportions of the aforesaid nutrient sources are not particularly restricted, and can be varied over a wide range. The optimum compositions and mixing proportions of nutrient sources for the antibiotic OA-6129-producing microorganisms can be easily determined by anyone skilled in the art through a simple small-scale experiment.

The nutrient medium may be sterilized prior to cultivation. Advantageously, the pH of the culture medium is adjusted to a range of 4 to 9, especially a range of 6 to 8, before or after sterilization.

Cultivation of antibiotic OA-6129-producing microorganisms in such culture media can, in principle, be carried out in accordance with methods usually employed for the production of antibiotics by actinomycetes. Usually, the cultivation is suitably carried out under aerobic conditions, for example, with stirring and/or forced aeration. Although the method of cultivation may be stationary, shaken or submerged with aeration and agitation, the submerged cultivation is advantageous.

The range of the cultivation temperature which can be used may be in any range of temperature, which does not substantially inhibit growth of the antibiotic OA-6129-producing microorganism but leads to the formation of the antibiotic OA-6129. The suitable cultivation temperature varies depending upon the microorganism to be used, and is generally 20° to 40° C., preferably 25° to 35° C.

For better antibiotic production, the pH of the culture broth may be adjusted to 4 to 9, especially 6 to 8, during cultivation.

In the case of large-scale fermentation intended for mass production, it is advantageous to perform seed cultivation before main fermentation by submerged cultivation in a production medium.

The cultivation can usually be continued until a substantial amount of antibiotic OA-6129 is accumulated in the broth. The cultivation period is usually 30 to 90 hours, although it varies depending upon the composition of the culture medium, the cultivation temperature, the microorganism used, etc.

Needless to say, everyone skilled in the art would be able to determine easily optimal cultivation conditions depending upon the properties of the particular microorganism used by performing simple experiments.

The amount of antibiotic OA-6129 accumulated in broth during cultivation can be measured by bioassay and bioautography, as described hereinafter. By these methods, the optimal amount of accumulation can be easily determined.

Antibiotic OA-6129 accumulated in the culture broth is water-soluble and is largely present extracellularly. Advantageously, the microbial cells are removed after cultivation by a known separating method such as filtration, centrifugation and extraction, and antibiotic OA-6129 is recovered from the resulting filtrate, supernatant, extract, and the like.

Depending upon the cultivation conditions used, the fermentation broth contains one or more of antibiotics OA-6129A,B and C, and the individual antibiotics can be isolated and purified by methods to be described hereinafter.

Although antibiotic OA-6129 can be isolated by various methods known per se, and methods frequently utilized for the isolation of carboxylic acid-type antibiotics can be advantageously applied. Examples of such methods are extraction at a low pH with a solvent such as ethyl acetate and n-butanol followed by transfer into an aqueous layer at a high pH; adsorption on activated carbon, Amberlite XAD (a registered trademark for a product of Rohm & Haas Co.), Diaion HP-20 (a registered trademark for a product of Mitsubishi Chemical Industries Ltd.), etc. followed by elution with methanol/water, acetone/water, etc.; adsorption on an ion exchange resin such as Dowex 1×2 (a registered trademark for a product of Dow Chemical Co.), QAE-Saphadex A-25 (a registered trademark for a product of Pharmacia Fine Chemicals AB), DEAE-Cellulose Whatman DE-32 (a registered trademark for a Product of Whatman Ltd.) and DEAE-Sephadex A-25 (a registered trademark for a product of Pharmacia Fine Chemicals AB) followed by elution; gel filtration on Sephadex G-10 (a registered trademark for a product of Pharmacia Fine Chemicals AB), Biogel P-2 (a registered trademark for a product of Bio-Rad Laboratories), etc.; column chromatography using cellulose, e.g. Avicel (a registered trademark for a product of American Viscose Corporation); forced precipitation by addition of a solvent such as acetone; and lyophilization. These methods can be used either singly or in combination. If required, they may be performed repeatedly. Antibiotic OA-6129C can be extracted by using a lipophilic ammonium salt and a water-immiscible solvent because it contains a hydroxysulfonyloxy group in the molecule. The substituted ammonium salt of antibiotic OA-6129C in the organic extract can be back-extracted into an aqueous layer using a solution of an alkali metal iodide such as sodium iodide.

The behaviors of antibiotics OA-6129 A, B and C during isolation and purification can be determined by bioassay and bioautography as described hereinbelow.

Thus antibiotic OA-6129 of formula (I-a) having the properties to be described hereinbelow can be obtained.

Antibiotic OA-6129 produced by the aforesaid fermentation method, i.e. the compounds of formula (I) in which $R_2$ is a hydrogen atom, are composed of antibiotic OA-6129A in which the hydrogen atoms at the 5- and 6-positions are in the trans configuration; antibiotic OA-6129B in which the hydrogen atoms at the 5- and 6-positions are in the cis or trans configuration; and antibiotic OA-6129C which is the 5,6-cis isomer.

The pantetheinyl group bonded to the carbon atom at the 3-position has one asymmetric carbon atom, and can be present in D-, L- or racemic form.

Antibiotic OA-6129 of formula (I-a) is generally more stable in salt form than in free form. Accordingly, it is preferred to handle them in the form of salts when they are to be used in pharmaceutical applications or as intermediates for conversion to new derivatives, or when they are to be subjected to the aforementioned purification steps.

Conversion of antibiotic OA-6129 into its salts can be performed by treating it with inorganic or organic bases in a manner known per se. Examples of inorganic or organic bases which can be used in salification include alkali metal hydroxides such as sodium hydroxide, potassium hydroxide and lithium hydroxide, alkaline earth metal hydroxides such as calcium hydroxide and magnesium hydroxide, and primary, secondary or tertiary organic amines such as monoethylamine, dimethylamine, trimethylamine, monoethanolamine, diethanolamine, benzathine and procaine.

If required, antibiotic OA-6129 obtained as above can be converted to its (unsubstituted or substituted benzyl) ester. The esterification can be carried out in a manner known per se. For example, the esterification can be performed by reacting antibiotic OA-6129 or its salts with an unsubstituted or substituted benzyl halide such as benzyl chloride, benzyl bromide, p-nitrobenzyl bromide, p-methoxybenzyl bromide, 2,4-dinitrobenzyl chloride and p-bromobenzyl bromide. The esterification is preferably carried out in an inert solvent. Examples of usable inert solvents include halogenated hydrocarbons such as chloroform and methylene chloride; amides such as dimethyl formamide and hexamethylphosphoramide; dimethyl sulfoxide; ethers such as tetrahydrofuran and dioxane; esters such as ethyl acetate and n-butyl acetate; and ketones such as acetone and methyl ethyl ketone. These solvents may be used singly or, as required, as a mixtures of two or more.

The reaction temperature is not critical, and can be varied widely depending upon the types of halide and solvent used. It may be selected from a range of temperatures at which antibiotic OA-6129 does not markedly decompose. It is generally not more than 60° C., preferably 0° to 40° C., more preferably 5° C. to room temperature.

If desired, a reaction promoter such as trimethylamine, triethylamine, pyridine or dicyclohexyl carbodiimide may be added during esterification.

Under these conditions, the reaction can be completed in about 1 to 24 hours, usually in 3 to 12 hours.

Antibiotic OA-6129 to be treated with halide may be crude, and cultivation broths or filtrates of antibiotic OA-6129-producing microorganisms, and partially purified preparations of antibiotic OA-6129 obtained by the above-described isolation and purification methods can be similarly esterified. Examples of such partially purified preparations are concentrated eluates from active carbon Diaion HP-20 (registered trademark); relatively pure concentrates obtained from the aforesaid eluates by QAE-Sephadex (a registered trademark) column chromatography using a concentration gradient of sodium chloride in phosphate buffer followed by desalting with active carbon; and concentrated solutions of butanol extracts recovered from cold culture broths at pH 3.5.

The resulting esters of antibiotic OA-6129 of formula (I-a) can be separated or purified by various methods known per se in the field of antibiotics. For example, after esterification, the reaction mixture is poured into an aqueous solution for removal of water-soluble impurities such as by-products. A neutral buffer is desirably used as the aqueous solution in order to maintain the pH of the reaction mixture substantially neutral. Then, the mixture is treated with a substantially water-immiscible nonpolar organic solvent such as ethyl acetate, benzene or chloroform to extract the ester of antibiotic OA-6129 into the organic solvent layer. The extraction efficiency in this step can be improved by utilizing the salting-out effect of a salt such as sodium chloride or ammonum sulfate.

After the solvent layer is dried over anhydrous sodium sulfate, the ester of antibiotic OA-6129 is isolated in a manner known per se. For example, gel filtration on Biobeads SX3 (a registered trademark for a product of Bio-Rad Laboratories), Sephadex LH-20 (a registered trademark for a product of Pharmacia Fine Chemicals AB), etc. and adsorptive chromatography on an adsorbent such as silica gel, alumina or Florisil (a registered trademark for a product of Floridin Co.), are suitably combined, and if desired, repeated.

Antibiotic OA-6129 of formula (I-a) and its salts of the present invention have a broad spectrum of antimicrobial activity. For example they have very strong anti-microbial activity against Gram-positive bacteria such as the genera Staphylococcus, Sarcina and Bacillus and Gram-negative bacteria such as the general Alkaligenes and Comamonas.

Antibiotic OA-6129 of formula (I-a) and its salts also show fairly striong antimicrobial activity against Gram-negative bacteria such as the genera Escherichia, Klevsiella and Proteus.

Antibiotic OA-6129 of formula (I-a) and its salts are characterized by the fact that they also exhibit relatively strong antimicrobial activity against Gram-negative bacteria such as the general Citrobacter, Proteus, Enterobacter, Klebsiella and Serratia which are known to be resistant to conventional $\beta$-lactam compounds.

The antimicrobial spectrum of antibiotic OA-6129 is demonstrated by its excellent minimum inhibitory concentrations (MIC) against various pathogenic test organisms given in Table 1 below.

The MIC is measured by an agar dilution method based on the standard method of the Japanese Society of Chemotherapy (Japanese Society of Chemotherapy: The Revised Method of Determination of MIC Values, Chemotherapy 22, 1126–1128, 1074). Specifically, the antibiotic is serially diluted with a 1/50 M phosphate buffer at a pH of 7.3 to prepare a twofold dilution series. One milliliter of each dilution and 9 ml of an agar medium (Heart Infusion Agar; a product of Difco Laboratories) are mixed and allowed to solidify in a Petri dish having a diameter of 9 cm. One loopful of the stock culture of the test microbe is inoculated in trypto-soy buillon (a product of Eiken Kagaku Co., Ltd.) and incubated at 37° C. for 18 hours. The resulting culture broth is diluted to a concentration of about $10^6$ cells/ml with physiological saline and inoculated on the agar plate by means of a microplanter. The inoculated agar plates are cultivated at 37° C. for 18 hours, and the MiC is defined as the lowest concentration of the antibiotic where the visible growth of the test microorganism is completely inhibited.

TABLE 1

MICs of antibiotics OA-6129 A, B$_1$, B$_2$ and C.

| Test organism | MIC ($\mu$g/ml) antibiotic | | | | | |
|---|---|---|---|---|---|---|
| | OA-6129A | OA-6129B$_1$ (5,6-cis) | OA-6129B$_2$ (5,6-trans) | OA-6129C | CEZ* | Ps-5** |
| Bacillus subtillis ATCC 6633 | 0.39 | 0.05 | 1.56 | 0.10 | 0.10 | 0.10 |
| Sarcina lutea S19 | 0.78 | 0.10 | 6.25 | 0.78 | 0.39 | 0.10 |
| Staphylococcus aureus 209P | 0.78 | 0.10 | 6.25 | 0.10 | 0.10 | 0.024 |
| S. aureus Smith | 1.56 | 1.56 | 12.5 | 0.78 | 0.20 | 0.20 |
| S. aureus Russell | 0.78 | 0.78 | 12.5 | 3.13 | 0.20 | 0.20 |
| S. epidermidis | 1.56 | 0.78 | 12.5 | 3.13 | 0.20 | 0.20 |
| Alcaligenes Faecolis A1 | 1.56 | 0.20 | 6.25 | 0.39 | 3.13 | 0.78 |
| Citrobacter Freundii GN346 | 50 | 6.25 | 25 | 50 | >400 | 3.13 |
| Comamonas terrigena B996 | 0.05 | 0.012 | 0.39 | 0.10 | 0.05 | 0.012 |
| Enterobacter aerogenes E19 | 25 | 3.13 | 25 | 6.25 | >400 | 3.13 |
| Ent. cloacae 45 | 50 | 6.25 | 50 | 50 | >400 | 3.13 |
| Ent. sp. E8 | 12.5 | 0.39 | 25 | 1.56 | 3.13 | 3.13 |
| Escherichia coli K-12 | 12.5 | 0.39 | 12.5 | 0.78 | 0.78 | 1.56 |
| E. coli RGN823 | 12.5 | 0.39 | 12.5 | 0.39 | 1.56 | 3.13 |
| Klebsiella pneumoniae K13 | 50 | >50 | 12.5 | 12.5 | 25 | 3.13 |
| Proteus mirabilis P6 | 50 | 0.78 | 50 | 0.78 | 3.13 | 6.25 |
| P. rettgeri P7 | 25 | 0.78 | 25 | 0.20 | 3.13 | 3.13 |
| P. vulgaris GN76 | 100 | 50 | 50 | 1.56 | >400 | 6.25 |
| P. sp. P22 | 100 | >50 | 50 | 0.78 | >400 | 6.25 |
| Providencia sp. P8 | 12.5 | 0.20 | 6.25 | 0.20 | 1.56 | 3.13 |
| Pseudomonas aenginosa IFO3445 | >100 | >50 | >100 | 50 | >400 | 12.5 |
| Ps. aeruginosa NCTC10490 | >100 | >50 | >100 | >50 | >400 | 12.5 |
| Serratia marcesceus S18 | 100 | 6.25 | 25 | 12.5 | >400 | 3.13 |

TABLE 1-continued

| | MICs of antibiotics OA-6129 A, B₁, B₂ and C. | | | | | |
|---|---|---|---|---|---|---|
| | MIC (μg/ml) antibiotic | | | | | |
| Test organism | OA-6129A | OA-6129B₁ (5,6-cis) | OA-6129B₂ (5,6-trans) | OA-6129C | CEZ* | Ps-5** |
| Ser. marcesceus T55 | 100 | 12.5 | 50 | 12.5 | >400 | 6.25 |

*CEZ = (cefazolin)

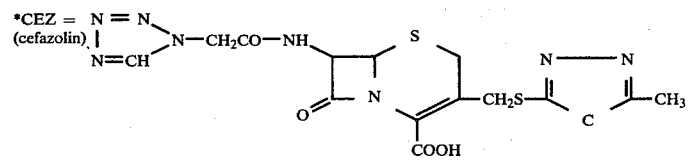

*PS-5 =

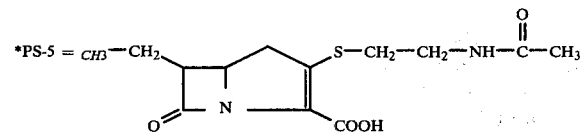

Antibiotic OA-6129 of formula (I-a) and its salts also have the ability to potentiate the antimicrobial activity of other antibiotics, especially known types of β-lactam antibiotics such as penicillins and cephalosporins, against β-lactamase-producing strains of microorganisms such as *Citrobacter freundii, Proteus vulgaris, Enterobacter aerogenes* and *Serratia marcescens*, and in many cases this effect is found to be synergistic.

The synergism of antibioitic OA-6129 with conventional β-lactam antibiotics is explicitly demonstrated by the following experiments (A) and (B).

(A) The synergistic effect on MIC of a combination of antibiotic OA-6129 with a known β-lactam compound is determined by using β-lactamase-producing bacteria in heart infusion broth (Difco) at an inoculum size of 10⁵ cells/ml in accordance with the microdilution transfer plate technique for determining in vitro synergy of antimicrobial agents (Antimicrob. Agents Chemother. 11, 225–228, 1977).

The results are given in Table 2.

TABLE 2

| FIC index of antibiotic OA-6129A combined with cephaloridine or aminobenzylpenicillin. | | | | |
|---|---|---|---|---|
| (1) *Citrobacter freundii* GN346 | | | | |
| Alone | | Combination | | FIC³ |
| OA-6129A | CER | OA-6129A | CER¹ | index |
| 50 μg/ml | 1250 μm/ml | 50 | <5 | — |
| | | 25 | <5 | 0.50 |
| | | 12.5 | 313 | 0.50 |
| | | 6.25 | 313 | 0.38 |
| | | 3.13 | 625 | 0.63 |
| | | 1.56 | 1250 | 1.03 |
| Alone | | Combination | | FIC³ |
| OA-6129A | ABPC | OA-6129A | ABPC² | index |
| 50 | 1250 | 50 | <5 | — |
| | | 25 | <5 | 0.50 |
| | | 12.5 | 313 | 0.50 |
| | | 6.25 | 313 | 0.38 |
| | | 3.13 | 625 | 0.63 |
| | | 1.56 | 1250 | 1.03 |
| (2) *Proteus vulgaris* GN76 | | | | |
| Alone | | Combination | | FIC³ index |
| OA6129A | CER | OA-6129A | CER¹ | μg/ml |
| 50 μg/ml | 1250 μg/ml | 50 | <5 | — |
| | | 25 | <5 | 0.50 |
| | | 12.5 | 20 | 0.27 |
| | | 6.25 | 39 | 0.16 |
| | | 3.13 | 156 | 0.19 |

TABLE 2-continued

| FIC index of antibiotic OA-6129A combined with cephaloridine or aminobenzylpenicillin. | | | | |
|---|---|---|---|---|
| | | 1.56 | 313 | 0.28 |
| Alone | | Combination | | FIC³ |
| OA6129A | ABPC | OA-6129A | ABPC² | index |
| 50 μg/ml | 1250 | 50 | <5 | — |
| | | 25 | 10 | 0.51 |
| | | 12.5 | 10 | 0.26 |
| | | 6.25 | 39 | 0.16 |
| | | 3.13 | 156 | 0.19 |
| 1.56 | 3.3 | 0.28 | | |

Note
¹CER: Cephaloridine

²ABPC: Aminobenzylpenicillin
³FIC index is defined as follows:

$$\frac{\left(\begin{array}{c}\text{MIC of antibiotic OA-6129A}\\\text{used in combination}\end{array}\right)}{\left(\begin{array}{c}\text{MIC of antibiotic OA-6129A}\\\text{used alone}\end{array}\right)} + \frac{\left(\begin{array}{c}\text{MIC of Cephaloridine}\\\text{or Ampivillin used in}\\\text{combination}\end{array}\right)}{\left(\begin{array}{c}\text{MIC of Cephaloridine}\\\text{or Ampivillin used}\\\text{alone}\end{array}\right)}$$

An FIC index of less than 0.5 indicates a synertistic effect and that of 0.5 to 1 means an additive effect, whereas antagonism is suggested by an FIC index of more than 1.

(B) The presence or absence of synergy is visually checked by the size difference in inhibitory zones observed when the test drug is disc-assayed on an agar plate of a detector microbe and on an agar plate of the detector containing cephaloridine or benzylpenicillin, respectively.

The experimental procedure and the results are shown below.

One loopful of the stock culture of a test organism is inoculated in heat infusion broth (5 ml/tube), and grown at 37° C. for 18 hours. The culture broth is diluted to a final concentration of about 10⁵ cells/ml in nutrient agar with or without benzyl penicillin or cephaloridine, and plated in a Petri dish with a diameter of 9 cm, as shown below.

|  | Amount of traditional β-lactam | Agar medium |
|---|---|---|
| Control | None (1 ml water) | 9 ml |
| PCG (*1) | 1 ml (500 μg/ml) | 9 ml |
| CER (*2) | 1 ml (500 μg/ml) | 9 ml |

Note:
(*1): PCG = benzylpenicillin
(*2): CER = cephaloridine

Using the above-prepared agar plates, antibiotic PS-5 (100 μg/ml), antibiotic OA-6129B$_2$ (5,6-trans OA-6129B) (100 μg/ml), benzylpenicillin (1000 μg/ml) and cephaloridine (1000 μg/ml) are subjected to disc assay. The results are shown in Table 3.

TABLE 3

Synergistic effect of antibiotic OA-6129B$_2$ combined with cephaloridine or benzylpenicillin. (the diameter of inhibition zones: mm)

| Microorganism | Drug | None | + CER | + PCG |
|---|---|---|---|---|
| Proteus vulgaris | OA-6129B$_2$ | 0 | 20.0 | 19.5 |
| GN76 | PS-5 | 17.5 | 23.5 | 25.0 |
|  | CER (1000 μg/ml) | 0 | 0 | 0 |
|  | PCG (1000 μg/ml) | 0 | 0 | 0 |
| Citrobacter | OA-6129B$_2$ | 12.0 | 16.0 | 13.0 |
| freundii GN346 | PS-5 | 22.5 | 24.0 | 23.5 |
|  | CER (1000 μg/ml) | 0 | 0 | 0 |
|  | PCG (1000 μg/ml) | 0 | 0 | 0 |
| Serratia | OA-6129B$_2$ | 12.0 | 22.0 | 12.0* |
| marcescens T55 | PS-5 | 23.5 | 34.0 | 24.0* |
|  | CER (1000 μg/ml) | 0 | 0 | 0* |
|  | PCG (1000 μg/ml) | tr. | 0 | tr.* |
| Enterobacter | OA-6129B$_2$ | 10.0 | 15.0 | 12.0 |
| cloacae 45 | PS-5 | 20.0 | 22.5 | 21.0 |
|  | CER (1000 μg/ml) | 0 | 0 | 0 |
|  | PCG (1000 μg/ml) | 0 | 0 | 0 |

*In this case, the concentration of benzylpenicillin was reduced to 5 μg/ml (final concentration).

When antibiotics OA-6129 A, B and C are intraperitoneally administered to ddY mice at a dose of 500 mg/kg, no acute toxicity is observed.

Antibiotics OA-6129 of formula (I-a) and its salts are more stable than other known carbapenem antibiotics, and their excellent stability is clearly seen from their half lives in phosphate buffers having various pH values.

By adding 2% sodium hydroxide or 10% hydrochloric acid, the pH of 0.05 M phosphate buffer is adjusted to 4, 5, 6, 7, 8 and 9, respectively, and distributed into test tubes in an amount of 3 ml. Concentrated solution of antibiotic OA-6129A (0.05 ml) is added to each test tube and allowed to stand in a thermostatic chamber of 28° C. The time course curve of the concentration decrease of antibiotic OA-6129A is drawn by spectrophotometric measurement at 300 nm, from which the half life of the antibiotic at the indicated pH is calculated. The results with antibiotic OA-6129A are shown in Table 4. As a control, antibiotic PS-5, a carbapenem compound described in the above-cited reference is simultaneously tested. Antibiotics OA-6129B and C have substantially the same stability as antibiotic OA-6129A.

TABLE 4

Stability of antibiotic OA-6129A at various pHs.

| | pH | | | | | |
|---|---|---|---|---|---|---|
| | 4 | 5 | 6 | 7 | 8 | 9 |
| Half life of OA-6129A (hours) | 1.05 | 4.07 | 21.2 | 57.7 | 128.4 | 132.2 |
| Half life of PS-5 (hours) | 0.20 | 3.43 | 13.2 | 38.2 | 78.0 | 36.2 |

Antibiotic OA-6129 and its salts have strong antimicrobial activity as stated above and thus are useful for the prevention and treatment of bacterial infections caused by Gram-positive and Gram-negative bacteria in not only human beings but also other animals such as mammals, poultry and fish.

Antibiotic OA-6129 and its salts may be administered orally, topically or parenterally (intravenously, intramuscularly, intraperitoneally, etc.). Depending upon the routes of administration, they can be used in a variety of conventional drug forms. For example, antibiotic OA-6129 and its salts can be formulated into solids (e.g., tablets, capsules, powders, granules, sugar-coated tablets, trouches, powder sprays, and suppositories), semi-solids (e.g., ointments, creams, semisolid capsles), or liquids (e.g. liquid preparations, emulsions, suspensions, lotions, syrups, preparations for injection, and liquid sprays) together with pharmaceutically acceptable carriers and diluents.

Unit dosage forms of antibiotic OA-6129 and its salts may generally contain 0.1 to 99% by weight, preferably 10 to 60% by weight, of the active ingredient irrespective of the type of formulation.

Methods of formulation are described below with typical carriers, excipients, diluents and other adjuvants.

Tablets and capsules for oral administration in unit dosage forms can be prepared with binders such as syrup, gum arabic, gelatin, sorbitol, tragacanth and polyvinyl pyrrolidone; excipients such as lactose, white sugar, starch, calcium phosphate, sorbitol and glycine; lubricants such as magnesium stearate, talc, polyethylene glycol and silica; disintegrants such as potato starch; and wetting agents such as sodium laurylsulfate. The tablets may be coated in a customary manner.

Liquid preparations for oral administration may take various forms such as oil or water suspensions, liquid preparations, emulsions and syrups. In addition, they may be served as dried products which can be mixed with water or other suitable carriers before use. These liquid preparations may usually contain such additives as suspending agents (e.g., sorbitol, syrup, methyl cellulose, sugar syrup, gelatin, hydroxyethyl cellulose, carboxymethyl cellulose, aluminum stearate gel and edible hydrogenated oils and fats), emulsifiers (e.g., lecithin, sorbitan monooleate and gum arabic), hydrophobic carriers (e.g., almond oil, fractionated coconut oil, oily esters, propylene glycol and ethyl alcohol), and preservatives (e.g., methyl p-hydroxybenzoate, propyl p-hydroxybenzoate and sorbate).

The suppositories may contain usual suppository bases such as cocoa butter and other glycerides.

The preparations for injection can be provided in unit dosage forms in ampoules or multi-dosage vessels containing preservatives. They may usually be in the form of suspensions, liquids or emulsions in oily or aqueous carriers, and may contain suspending agents, stabilizeres and/or dissolving aids. Alternatively, the active component may be in the form of a powder which can be formulated by dissolving it in pyrogen-free sterile water prior to use.

Antibiotic OA-6129 and its salts may also be formulated into forms suitable for absorption through the nasal, pharyngolaryngeal and mucosa, for example powder sprays, liquid sprays, inhalations, trouches, and gargles. Pharmaceutical formulation for ophthalmological and otological uses may be provided as liquid or simisolid capsules or drops. Topical drugs may include ointments, creams, lotions, coating agents, etc. and can be formulated by using hydrophobic or hydrophilic bases.

The above preparations may contain stabilizers, binders, antioxidants, preservatives, lubricants, suspending agents, thickeners, flavoring agents and buffers.

When antibiotic OA-6129 and its salts are to be for treatment of animals such as chicken, cattle, swine and sheep, they may be formulated into intramammary preparations by using long-acting or quick-releasing bases, or prepared as feed additive concentrates in a known manner.

The various forms of drugs provided by this invention may contain antibiotic QA-6129 and its salts as sole active principles, or may further contain other therapeutically useful active ingredients.

Since antibiotic OA-6129 and its salts have the ability to synergistically increase the antimicrobial activity of conventional $\beta$-lactam compounds against $\beta$-lactamase-producing microorganisms as stated hereinabove, it may be used in combination with known types of $\beta$-lactam antibiotics. Examples of such $\beta$-lactam antibiotics include penicillin derivatives such as benzylpenicillin, phenoxymethylpenicillin, carbenicillin, ampicillin and amoxicillin; and cephalosporin derivatives such as cephaloridine, cephalothin, cefazolin, cephalexin, cefoxitin, cephacetrile, cephamandole, cephapirin, cephradine and cephaloglycin.

When antibiotic OA-6129 and its salts are to be used in combination with the aforesaid $\beta$-lactam antibiotics, the ratio of antibiotic OA-6129 to conventional $\beta$-lactam is not critical, and can be varied over a wide range. Generally, the weight ratio of antibiotic OA-6129 and its salts to conventional $\beta$-lactam antibiotic is from 20:1 to 1:150, preferably from 10:1 to 1:100.

The dose of antibiotic OA-6129 and its salts can be varied widely depending upon the gravity of affection, general conditions and body weight of the subject to be treated, the type of infection, the route of administration, and the number of daily dosage. It is usually advantageous that 0.05 to 500 mg/kg body weight/day, preferably 0.5 to 200 mg/kg body weight/day, of antibiotic OA-6129 and its salts is given in single or multiple doses. The dose may fall outside the specified range based upon the judgement of the responsible physician, the physical difference among individual subjects, and the severity of infection.

Antibiotic OA-6129 and its salts can be used not only in the aforesaid forms, but also can be directly included into animal feeds or used as animal feed additives. They also can find utility in preparation of germicides and antiseptics for food preservation.

The following Examples illustrate the present invention more specifically. The qualitative and quantitative analysis of the antimicrobially active substances mentioned in the following Examples were performed by the following methods.

(1) Bioassay

An overnight culture of *Comamonas terrigena* B-996 on nutrient agar was diluted in nutrient broth to give a seed cell suspension which had an optical density of 0.04 at 610 nm. One percent of the seed cell suspension was inoculated in molten agar medium consisting of 0.8% Kyokuto Nutrient Broth Powder (a product of Kyokuto Seiyaku Kogyo Kabushiki Kaisha) and 1% of Bacto-Agar (a product of Difco Laboratories). Seven milliliters of the inoculated molten agar was put into a Petri dish having a diameter of 9 cm and solidified to provide a Comamonas assay plate.

(2) Bioautography

Instead of the 9 cm Petri dish, a 32×24 cm tray was filled with 100 ml of the inoculated molten agar medium to give a large bioassay plate for bioautography.

A sheet of chromatographic filter paper on which antimicrobial compounds had been developed in a suitable solvent system was kept in contact with the surface of the agar for 15 minutes. After the chromatogram was removed, the large assay plate was cultivated at 35° C. for 20 hours. The Rf value of an antimicrobial substance was calculated from the position of the inhibition zone (qualitative), and the relative amount of the active substance can be semi-quantitatively determined from the size of the inhibitory zone.

When a thin-layer chromatographic plate is to be bioautographed, the plate was kept in contact with the surface of the agar through a sheet of thin paper for 15 minutes so that the thin layer of silica gel not be left on the assay plate. As explained above, the qualitative and semi-quantitative analyses could be performed with thin layer chromatograms, too.

EXAMPLE 1

Fermentative production and purification of antibiotic OA-6129:

(A) A seed culture medium S-1 having the following composition (100 ml) was put into a 500 ml Erlenmeyer flask, and sterilized in a customary manner at 120° C. for 15 minutes.

One loopful of mature spores of Streptomyces sp. OA-6129 was inoculated in the seed culture medium, and cultivated under shaking at 28° C. for 48 hours on a rotary shaker (200 rpm, throw 3.5 cm). Two flasks of the resulting seed culture were transferred in a 30-liter jar fermentor containing 15 liters of seed culture medium SE-4 (see below), and aerobically cultivated at 28° C. at an aeration rate of 7.5 liters/min. with stirring at 400 rpm. As an antifoamer, 0.07% of Silicone KM-75 (a registered trademark for a product of Shin-etsu Chemical Co., Ltd.) was added.

(B) Two liters of the 24 hour-old seed culture in medium SE-4 was inoculated in a 200-liter fermentor containing 100 liters of production medium GM-1 (see below) and aerobically cultured at 28° C. for 90 hours at an aeration rate of 50 liters/min. with agitation at 200 rpm. Silicone KM-75 (registered trademark) was added in an amount of 0.07% for prevention of foaming.

The culture broth was sampled at the indicated times and centrifuged for bioassay of the antimicrobial activity in the supernatant.

The results are tabulated below.

| Cultivation time (hours) | Antimicrobial titer ($\mu$g/ml)* |
|---|---|
| 48 | 2.6 |
| 72 | 11.5 |
| 90 | 24.0 |

| Seed culture medium S-1 | |
|---|---|
| Soybean meal | 1.5% (W/V) |
| Yeast extract | 0.5 |
| Potato starch | 2.0 |
| CaCO$_3$ | 0.2 |
| pH (before sterilization) | 7.0 |
| Seed culture medium SE-4 | |
| Meat extract | 0.3% (W/V) |
| Tryptone | 0.5 |
| Glucose | 0.1 |
| Soluble starch | 2.4 |
| Yeast extract | 0.5 |
| CaCO$_3$ | 0.4 |
| Soybean meal | 0.5 |
| pH (before sterilization) | 7.5 |
| Culture medium GM-1 | |
| Glycerin | 8.0% (W/V) |
| Fishmeal | 1.0 |
| Soybean meal | 3.0 |
| CaCO$_3$ | 0.3 |
| K$_2$HPO$_4$ | 0.2 |
| MgSO$_4$ | 0.2 |
| pH (adjusted with NaOH before sterilization) | 7.5 |

*PS-5 sodium salt was employed as a tentative bioassay standard.

Vitamin B$_{12}$ in 0.01 M phosphate buffer, pH 5.5, was separately autoclaved for 5 minutes at a pressure of 1 kg/cm$^2$.G and added in an amount of 0.0005% (W/V).

(C) Topco Perlite No. 34 (a registered trademark for a product of Toko Perlite Kabushiki Kaisha) was added in an amount of 5% (W/V) to 100 liters of the 90-hour old fermentation broth. The suspension was centrifuged with a basket-type centrifugal separator to give 90 liters of the broth filtrate. The broth filtrate was adsorbed on a column (15×100 cm) of Diaion HP-20 (registered trademark). The column was washed with 5 liters of distilled water, and eluted with 30% (W/V) aqueous acetone. The eluate was fractionated in 1.0 liter volumes. Antimicrobial active fractions Nos. 8 to 15 (8.0 liters in total) were collected, and adsorbed on a column (8×60 cm) of Diaion PA306S (a registered trademark for a product of Mitsubishi Chemical Industries Ltd.). The column was washed with 1.0 liter of distilled water and then eluted with 3.0% sodium chloride. All 500 fractions were bioassayed by *Comamonas terrigena* B996 and active fractions Nos. 7 to 16 (5.0 liters in total) which contained antibiotics OA-6129 A, B$_1$ and B$_2$ were collected. The said PA306S column was then eluted with 30% sodium chloride to yield 7.0 liters in total of active fractions Nos. 3 to 16 which contained antibiotic OA-6129C.

Sodium chloride (300 g) was added to 5.0 liters of the PA306S eluate containing antibiotics OA-6129 A, B$_1$ and B$_2$, and passed through a column (6×150 cm) of Diaion HP-20 (registered trademark). The column was washed with 500 ml of distilled water and eluted with 4.0 liters in total of aqueous acetone by using a linear concentration gradient of acetone from 0 to 40%. The eluate was divided into 17 ml fractions. Antimicrobially active fractions Nos. 20 to 130 (about 1.8 liters in total) contained antibiotics OA-6129 B$_1$ and B$_2$ as main components together with a small amount of antibiotic OA-6129A. The subsequent antimicrobially active fractions Nos. 131 to 170 (700 ml) contained antibiotic OA-6129A.

These two solutions were respectively lyophilized to form dark brown powders.

(D) Purification of antibiotic OA-6129A

The dark brown lyophilisate of antibiotic OA-6129A was dissolved in a small amount of distilled water, and charged onto a column (8×100 cm) of Biogel P-2 (registered trademark). The column was developed with distilled water, and antimicrobially active fractions (1.0 liter) were collected. The active fractions were combined and charged on a column (4×40 cm) of QAE-Sephadex A-25 (registered trademark) which had been equilibrated with 0.01 M phosphate buffer, pH 8.4. The column was washed with 200 ml of the buffer, and then eluted with a linear concentration gradient of sodium chloride from 0 to 4% in 3.0 liters of the buffer. The eluate was collected in 15 ml portions and subjected to bioassay. Active fractions Nos. 51 to 70 (300 ml) were combined and lyophilized to give yellowish brown powder. This powder was dissolved in a small amount of distilled water, and 5 g of sodium chloride was added. The solution was adsorbed on a column (2×50 cm) of Diaion HP-20AG (a registered trademark for a product of Mitsubishi Chemical Industries Ltd.). The column was rinsed with 50 ml of 5% sodium chloride and then with 100 ml of distilled water, and eluted with a linear a concentration gradient of acetone from 0 to 30% in a total volume of 1.0 liter. The eluate wad divided into 10 ml. fractions. By bioassay, active fractions Nos. 35 to 45 (110 ml) were collected and lyophilized to give 52 mg of yellowish brown crude powder of antibiotic OA-6129A.

This powder was dissolved in a small amount of distilled water, and the solution was charged onto a column (2×80 cm) of Sephadex G-10 (registered trademark). The column was developed with distilled water and 30 ml of antimicrobially active eluate was collected. The active eluate was applied on a QAE-Sephadex A-25 (registered trademark) column (2×30 cm) which had been equilibrated with 0.01 M phosphate buffer, pH 8.4. The column was washed with 50 ml of the buffer, and eluted with a linear concentration gradient of sodium chloride from 0 to 5% in 800 ml of the phosphate buffer. The eluate was fractionated in 5 ml portions, and active fractions Nos. 36 to 40 (25 ml) were collected by bioassay.

Four grams of sodium chloride was added to the combined fractions and charged on a column (2×40 cm) of Diaion HP-20AG (registered trademark). The column was washed with 50 ml of distilled water, and eluted with a linear concentration gradient of acetone from 0 to 30% in a total volume of 800 ml. The eluate was fractionated in 5 ml portions. Active fractions Nos. 105 to 117 (65 ml) were collected by bioassay and lyophilized to give 21 mg of pale yellow powder of antibiotic OA-6129A.

The resulting sample of antibiotic OA-6129A showed the following properties.

(1) Form: pale yellow powder.

(2) Specific rotation $[\alpha]_D^{24}$: 11.6° (c=1.0, 0.01 M phosphate buffer, pH 8.4).

The specific rotation was determined on the assumption that $\epsilon$ at $\lambda_{max}$300 nm was 5600.

(3) Molecular formula: Theoretical molecular formula C$_{20}$H$_{30}$N$_3$O$_7$SNa (M.W.=479).

(4) Ultraviolet absorption spectrum 0.01 M phosphate buffer (pH 8.4)

$\lambda_{max}$ nm ($\epsilon$): 300 (5600).

(5) Main peaks in the infrared absorption spectrum KBr): $\nu_{max}^{KBr}$ cm$^{-1}$: 1760 ($\beta$-lactam), 1660 (amide), 1600 (carboxylate).

(B 6) Nuclear magnetic resonance spectrum (solvent D$_2$O, internal standard DSS) $\delta$(ppm):

$$0.89 \text{ (3H, s, CH}_3-\underset{\underset{CH_3}{|}}{C}-), 0.92 \text{ (3H, s, CH}_3-\underset{\underset{CH_3}{|}}{C}-),$$

1.00 (3H, t, J = 7.5Hz, CH$_2$—CH$_3$), 1.60-2.00 (2H, m, CH$_2$—CH$_3$), 2.48 (2H, t, J = 6.5 Hz, N—CH$_2$—CH$_2$—CO), 2.80-3.65 (11H, m, C—4H$_2$, C—6H,

S—CH$_2$—CH$_2$—N, N—CH$_2$—CH$_2$—CO, C—CH$_2$—OH), $$3.95 \text{ (2H, m, C—5H, HO}-\underset{\underset{|}{}}{CH}-\text{CO}).$$

(7) Paper chromatography
Toyo Filter Paper No. 50
Developing solvent: Acetonitrile/water (8/2)
Detection method: Bioautography by *Comamonas terrigena* B996
Rf value: 0.53

(8) Color reactions
Reaction with ninhydrin: negative
Reaction with Ehrlich's reagent: positive (9) Elemental analysis and melting point measurement impossible because of the hygroscopic nature of the sample.

(E) Purification of antibiotics OA-6129 B$_1$ and B$_2$

The dark brown powder of antibiotics OA-6129 B$_1$ and B$_2$ obtained in step (C) was dissolved in a small amount of distilled water, and charged onto a column (8×100 cm) of Biogel P-2 (registered trademark). The column was developed with distilled water. Active fractions (1.0 liter in total) were collected by bioassay and adsorbed on a column (4×40 cm) of QAE-Sephadex A-25 (registered trademark) which had been equilibrated with 0.01 M phosphate, p.H 8.4. The column was washed with 200 ml of 0.01 M phosphate buffer, pH 8.4, and eluted with a linear concentration gradient of sodium chloride from 0 to 4% in 3.0 liters of the phosphate buffer. The eluate was fractionated in 15 ml portions, and antimicrobially active fractions Nos. 51 to 70 (300 ml) were collected. The combined fractions were lyophilized to give yellowish brown powder of antibiotics OA-6129B$_1$ and B$_2$. The powder was dissolved in a small amount of distilled water, and 5 g of sodium chloride was added. The solution was adsorbed on a column (2×50 cm) of Diaion HP-20AG (registered trademark). The column was washed with 50 ml of 5% sodium chloride and then with 100 ml of distilled water and eluted by using a linear concentration gradient of acetone from 0 to 30% in a total volume of 1.0 liter. The eluate was fractionated in 10 ml portions, and monitored by bioassay. Active fractions Nos. 15 to 24 (100 ml) and active fractions Nos. 26 to 35 (100 ml) were collected and combined respectively. The former solution contained antibiotic OA-6129B$_1$, and the latter antibiotic OA-6129B$_2$. Lyophilization of these solutions gave 840 mg of yellowish powder of antibiotic OA-6129B$_1$ and 470 mg of yellowish brown powder of antibiotic OA-6129B$_2$, respectively.

(F) Purification of the antibiotic OA-6129B$_1$

The crude powder of antibiotic OA-6129B$_1$ (840 mg) was dissolved in a small amount of distilled water, and charged onto a column (2×80 cm) of Sephadex G-10 (registered trademark). The column was developed with distilled water, and the bioassay provided 35 ml of active fractions. The active fractions were combined and adsorbed on a column (2×30 cm) of QAE-Sephadex A-25 (registered trademark) which had been equilibrated with 0.01 M phosphate buffer, pH 8.4. The column was washed with 50 ml of the above buffer, and eluted with a linearly increasing concentration of, sodium chloride from 0 to 5% in 800 ml of the buffer. Five 5 ml fractions-from Nos. 39 to 43 which had an ultraviolet absorption maximum at 300 nm were collected and combined. The solution was mixed with 4 g of sodium chloride, and then adsorbed on a column (2×40 cm) of Diaion HP-20AG (registered trademark). The column was developed with distilled water, and the eluate was recovered in 5 ml fractions. By checking for an ultraviolet absorption maximum at 300 nm fractions Nos. 51 to 70 (100 ml) were collected. These fractions were united and lyophilized to give 21 mg of pale yellow powder of antibiotic OA-6129B$_1$.

The pale yellow powder of OA-6129B$_1$ (21 mg) was dissolved in a small amount of distilled water, and the solution was adsorbed on a column (1.5×7 cm) of active carbon (a product of Wako Pure Chemical Industries, Ltd.). The column was washed with 20 ml of distilled water and then eluted by increasing linearly the concentration of isopropanol from 0 to 50% in a total volume of 200 ml. The eluate was fractionated in 2 ml portions. Active fractions Nos. 18 to 32 (30 ml) which had an ultraviolet absorption maximum at 300 nm were collected, and lyophilized to give 8 mg of pale yellow powder of pure antibiotic OA-6129B$_1$.

The lyophilized preparation of antibiotic OA-6129B$_1$ showed the following properties.

(1) Form: Pale yellow powder.
(2) Specific rotation [α]$_D^{24}$: 24.2° (c=0.5, H$_2$O).
(3) Molecular formula: C$_{20}$H$_{30}$N$_3$O$_8$SNa (M.W.=495).
(4) Ultraviolet absorption spectrum: λ$_{max}^{H2O}$·nm (ε): 300 (6400).
(5) Main peaks in the infrared absorption spectrum: ν$_{max}^{KBr}$ cm$^{-1}$: 1750 (β-lactam), 1650 (amide), 1590 (carboxylate).
(6) Nuclear magnetic resonance spectrum (solvent D$_2$O, internal standard DSS) δppm:

$$0.86 \text{ (3H, s, CH}_3-\underset{\underset{CH_3}{|}}{C}-), 0.89 \text{ (3H, s, CH}_3-\underset{\underset{CH_3}{|}}{C}-),$$

$$1.33 \text{ (3H, d, J = 6.0Hz, CH}_3-\underset{\underset{|}{OH}}{CH}-),$$

2.47 (2H, t, J = 6.5Hz, NH—CH$_2$—CH$_2$—CO), 2.75-3.70 (11H, m, C—4H$_2$, C—6H, $$\text{S—CH}_2\text{—CH}_2\text{—NH, NH—CH}_2\text{—CH}_2\text{—CO, }-\underset{\underset{|}{}}{\overset{|}{C}}-\text{CH}_2\text{—OH}),$$

$$3.93 \text{ (1H, s, HO}-\underset{\underset{|}{}}{CH}-\text{CO}),$$

$$3.95\text{-}4.40 \text{ (2H, m, C—5H, CH}_3-\underset{\underset{|}{OH}}{CH}-).$$

(7) Paper chromatography
Toyo Filter Paper No. 50
Developing solvent: Acetonitrile/0.1 M tris(hydroxymethyl)-aminomethane hydrochloride buffer, pH 7.5/0.1 M ethylene diamine tetracetate, pH 7.5 = 120/30/1

Detection method: Bioautography by *Comamonas terrigena* B996.

Rf value: 0.17

(8) High voltage paper electrophoresis.

Electrophoresis was performed at 1500 V for 30 minutes using Veronal buffer, pH 8.6, and Toyo Filter Paper No. 51. The Rm value was 0.67, when the relative mobility of PS-5 sodium salt was taken as 1.0.

(9) High-performance liquid chromatography

Packing material: $\mu$-Bondpack $C_{18}$

Column: 7.8 mm (internal diameter)×30 cm (Nihon Waters Ltd.)

Mobile phase: 0.01 M diammonium phosphate buffer, pH 7.5, containing 3% acetonitrile Flow rate: 1.5 ml/min.

Detection method: ULtraviolet absorption at 301 nm.

Under the above conditions, the retention time was 13.9 minutes.

(G) Purification of antibiotic OA-6129B$_2$

The crude powder of antibiotic OA-6129B$_2$ (470 mg) obtained in step (E) was dissolved in a small amount of distilled water, and the solution was charged onto a column (2×80 cm) of Sephadex G-10 (registered trademark). The column was developed with distilled water, and 30 ml of the active eluate was collected by bioassay. The active eluate was adsorbed on a column (2×30 cm) of QAE-Sephadex A-25 (registered trademark) which had been equilibrated with 0.01 M phosphate buffer, pH 8.4. The column was washed with 50 ml of the phosphate buffer and eluted with a linear concentration gradient of sodium chloride from 0 to 5% in 800 ml of the phosphate buffer. Seven 5 ml fractions from Nos. 35 to 41 which had an ultraviolet absorption maximum at 300 nm were collected, combined and mixed with 4 g of sodium chloride. The solution was adsorbed on a column (2×40 cm) of Diaion HP-20AG (registered trademark). The column was washed with 50 ml of distilled water and eluted by increasing linearly the concentration of acetone from 0 to 20% in a total volume of 800 ml. The eluate was fractionated in 5 ml portions and monitored by ultraviolet spectrometry at 300 nm. Active fractions Nos. 112 to 125 (70 ml) were collected and combined. The solution was lyophilized to give 23 mg of pale yellow powder of pure antibiotic OA-6129B$_2$.

The lyophilized sample of antibiotic OA-6129B$_2$ showed the following properties.

(1) Form: pale yellow powder.

(2) Specific rotation $[\alpha]_D^{24}$: 14.7° (c=1.0, 0.01 M phosphate buffer, pH 8.4).

(3) Molecular formula: $C_{20}H_{30}N_3O_8SNa$ (M.W.=495).

(4) Ultraviolet absorption spectrum: 0.01 M phospate buffer (pH 8.4) $\lambda_{max}$·nm ($\epsilon$)=300 (5400).

(5) Main peaks in the infrared absorption spectrum: $\nu_{max}^{KBr}$ cm$^{-1}$: 1760 ($\beta$-lactam), 1660 (amide), 1600 (carboxylate).

(6) Nuclear magnetic resonance spectrum (solvent D$_2$O, internal standard DSS) $\delta$ ppm:

0.87 (3H, s, $CH_3-\overset{|}{\underset{|}{C}}-$) 0.92 (3H, s, $CH_3-\overset{|}{\underset{|}{C}}-$), 1.28 (3H, d, J = 7.0Hz, $CH_3-\overset{OH}{\underset{|}{CH}}-$), -continued 2.45 (2H, t, J = 6.5Hz, $NH-CH_2-CH_2-CO$), 2.75–3.60 (11H, m, C—4H$_2$, C—6H, $S-CH_2-CH_2-NH$, $NH-CH_2-CH_2-CO$, $-\overset{|}{\underset{|}{C}}-CH_2-OH$), 3.94 (1H, s, $HO-\overset{|}{CH}-CO$), 3.95–4.35 (2H, m, C—5H, $CH_3-\overset{OH}{\underset{|}{CH}}-$).

(7) Paper chromatography

Toyo Filter Paper No. 50

Developing solvent: Acetonitrile/0.1 M tris(hydroxymethyl)aminomethane hydrochloride buffer, pH 7.5/0.1 M ethylenediamine tetraacetate, pH 7.5 = 120/30/1

Detection method: Bioautography by *Comamonas terrigena* B996

Rf value: 0.17

(8) High voltage paper electrophoresis

Electrophoresis was carried out at 1500 V for 30 minutes using Veronal buffer, pH 8.6, and Toyo Filter Paper No. 51. The Rm value (relative to the mobility of PS-5 sodium salt) was 0.67.

(9) High performance liquid chromatography

Packing material: $\mu$-Bandpack $C_{18}$

Column: 7.8 mm (internal diameter)×30 cm (Nihon Waters Ltd.)

Mobile phase: 0.01 M diammonium phosphate buffer, pH 7.5, containing 3% acetonitrile Flow rate: 1.5 ml/min.

Detection method: Ultraviolet absorption at 301 nm

Under the above conditions, the retention time was 22.5 minutes.

(H) Purification of antibiotic OA-6129C

The aforesaid eluate of antibiotic OA-6129C obtained in step (C) was adsorbed on a column (5×80 cm) of Diaion HP-20 (registered trademark). The column was washed with 1.5 liters of 0.01 M phosphate buffer, pH 8.4, and eluted with a linear acetone concentration gradient from 0 to 20% in a total volume of 6.0 liters. Five 250 ml fractions from Nos. 9 to 13 were collected and combined.

The solution was subjected to extraction with 1.0 liter of methylene chloride containing 3% alkyldimethylbenzylammonium chloride (a product of Tokyo Chemical Industry Co., Ltd.). The methylene chloride layer was separated and extracted with 300 ml of 8% sodium iodide. The aqueous extract was charged onto a column (8×100 cm) of Biogel P-2 (registered trademark) which had been equilibrated with 0.01 M phosphate buffer, pH 8.4, and the column was developed with the same buffer to provide, 1.2 liters of the microbially active eluate.

The active eluate was adsorbed on a column (4×60 cm) of Diaion HP-20 (registered trademark), and the column was rinsed with 600 ml of distilled water and eluted by increasing linear by the concentration of acetone from 0 to 10% in a total volume of 3.0 liters. The eluate were fractionated in 15 ml portions. The bioassay permitted the collection of active fractions Nos. 41 to 115 (1.1 liters). These active fractions were combined and adsorbed on a column (4×40 cm) of QAE- Sephadex A-25 (registered trademark) which had been equilibrated with 0.01 M phosphate buffer, pH.8.4. The column was washed with 500 ml of the above buffer, and eluted with a linearly increasing concentration of sodium chloride from 0 to 5% in 3.0 liters of the phosphate buffer. The eluate was recovered in 15 ml fractions, and active fractions Nos. 112 to 139 (420 ml) were collected by bioassay. Sodium chloride was added to the combined active fractions to make a final concentration of 5%. The solution was adsorbed on a column (3×60 cm) of Diaion HP-20 AG (registered trademark), and the column was eluted with deionized water. The eluate was fractionated in 15 ml volumes, and active fractions Nos. 31 to 48 (270 ml) were collected by bioassay. These active fractions were combined and lyophilized to give 135 mg of yellowish brown powder. The powder was dissolved in a small amount of distilled water, and charge onto a column (2×70 cm) of Sephadex G-10 (registered trademark). The column was developed with distilled water, and active fractions (60 ml) were collected under antimicrobial monitoring.

These active fractions were combined and then adsorbed on a column (4×30 cm) of QAE-Sephadex A-25 (registered trademark) which had been equilibrated with 0.01 M phosphate buffer, pH 8.4. The column was washed with 800 ml of the said phosphate buffer, and eluted with a linear concentration gradient of sodium chloride from 0 to 5% in 2.4 liters of the phosphate buffer. Antimicrobially active fractions Nos. 118 to 139 (286 ml) were collected.

Sodium chloride was added to the combined fractions to reach a final concentration of 5%. The solution was adsorbed on a column (3×650 cm) of Diaion HP-20AG (registered trademark), and the column was eluted with deionized water. The eluates were fractionated in 10 ml volumes. Fractions which had an ultraviolet absorption maximum at 300 nm were collected and combined to give 90 ml of antibiotic OA-6129C solution.

The solution was lyophilized to give 18 mg of pale yellow powder of antibiotic OA-6129C.

The resulting preparation of antibiotic OA-6129C showed the following properties.

(1) Form: Pale yellow powder.
(2) Specific rotation $[\alpha]_D^{24}$: 17.4° (c=0.55, 0.01 M phosphate buffer, pH 8.2).
(3) Elemental analysis for $C_{20}H_{29}N_3O_{11}S_2Na_2 \cdot 2H_2O$:

|  | C | H | N | S |
|---|---|---|---|---|
| Calculated (%) | 37.91 | 5.25 | 6.63 | 10.12 |
| Found (%) | 37.61 | 5.00 | 6.38 | 9.52 |

(4) Molecular weight: 597.5731 (molecular formula $C_{20}H_{29}N_3O_{11}S_2Na_2$)
(5) Ultraviolet absorption spectrum (in 0.01 M phosphate buffer, pH 8.2): $\lambda_{max}$ nm ($\epsilon$): 300.5 (7600).

(6) Main peaks in the infrared absorption spectrum (KBr): $\nu_{max}^{KBr}$ cm$^{-1}$: 1750 ($\beta$-lactam), 1660–1595 (amide, carboxylate), 1250–1220 (sulfate ester)

(7) Nuclear magnetic resonance spectrum (solvent $D_2O$; internal standard DSS): $\delta$ ppm:

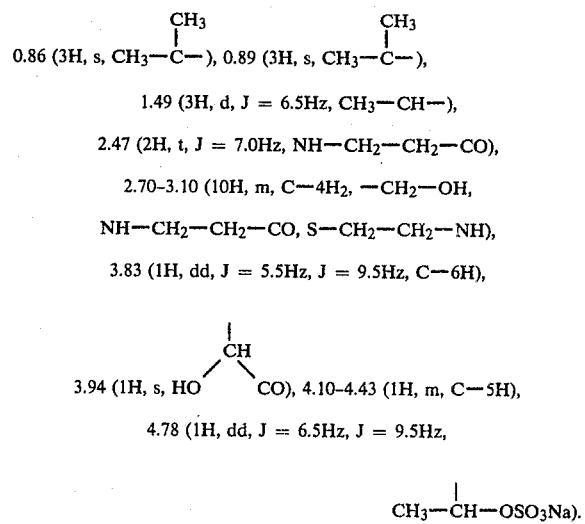

(8) Paper chromatography
Toyo Filter Paper No. 50
Developing solvent: Acetonitrile/0.1 M tris(hydroxymethyl)aminomethane hydrochloride buffer (pH 7.5)/0.1 M sodium ethylenediaminetetraacetate (pH 7.5)=120/30/1
Detecting method: Bioautography by *Comamonas terrigena* B996
Rf value: 0.09 (Rf value of PS-5=0.31)
(9) High voltage paper electrophoresis
Electrophoresis was carried out at 1500 V for 30 minutes using Veronal buffer, pH 8.6, and Toyo Filter Paper No. 51. The Rm value was 1.69, when the relative mobility of PS-5 sodium salt was taken at 1.0.
(10) Color reactions:
Reaction with ninhydrin: negative
Reaction with Ehrlich's reagent: positive
(11) Hydrolysisate (6 N HCl, 115° C., 19 hours)
By filter paper electrophoresis (3000 V, 20 minutes) in formic acid-acetic acid buffer, pH 1.8, the formation of cysteamine (Rm=2.26) and $\beta$-alanine (Rm=1.53) was confirmed. (The Rm values were relative to the mobility of alanine as 1.0.)

From the foregoing physicochemical properties, it is concluded that the planar structure of antibiotic OS-6129C is

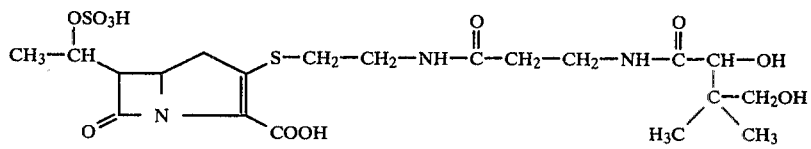

with the 5,6-cis configuration.

EXAMPLE 2

Production of benzyl ester of antibiotic OA-6129A:
Sodium salt of antibiotic OA-6129A (44.6 mg) was dissolved in 80 ml of dimethyl formamide. Under ice-cooling, 0.25 ml of triethylamine and then 0.18 ml of benzyl bromide were added with stirring. The reaction was performed for 30 minutes at the said temperature, and then for 3 hours at room temperature.

The reaction mixture was poured into 100 ml of ethyl acetate. The solution was washed with 20 ml of saturated sodium chloride solution in 0.01 M phosphate buffer, pH 8.4. The aqueous layer was separated and extracted with 100 ml of methylene chloride. The methylene chloride extract and the ethyl acetate layer were combined, dehydrated over anhydrous sodium sulfate, and distilled under reduced pressure. The residue was dissolved in a small amount of benzene, and the solution was adsorbed on a column of Biobeads SX-3 (registered trademark). The column was eluted with benzene. By silica gel thin-layer chromatography using a 1:1 mixture of benzene and acetone, fractions which showed an ultraviolet absorptive spot at Rf 0.39 were collected, and concentrated to dryness under reduced pressure.

The residue was dissolved in a small amount of methylene chloride, and charged on a column of 12 g silica gel. The column was developed successively with benzene/acetone (2/1), benzene/acetone (1/1), benzene/acetone (1/3), and acetone. The acetone eluate was recovered and evaporated under reduced pressure to give 21.4 mg of the title compound.

The benzyl ester of antibiotic OA-6129A showed the following physico-chemical properties.

(1) Specific rotation $[\alpha]_D^{24}$: 31.5° (c=1.0, $CH_2Cl_2$).

(2) Ultraviolet absorption spectrum: $\lambda_{max}^{CH2Cl2}$ nm ($\epsilon$): 318 (7400).

(3) Main peaks in the infrared absorption spectrum: $\nu_{max}^{CH2Cl2}$ cm$^{-1}$: 1772 ($\beta$-lactam), 1700 (ester), 1665 (amide).

(4) Nuclear magnetic resonance spectrum (internal standard TMS): (a) When the solvent was $CD_2Cl_2$: δ (ppm):

0.88 (3H, s, CH$_3$—C—), 0.97 (3H, s, CH$_2$—C—), 1.03 (3H, t, J = 7.5Hz, CH$_2$—CH$_3$), 1.60–2.10 (3H, m, CH$_2$—CH$_2$, OH), 2.39 (2H, t, J = 6.5Hz, N—CH$_2$—CH$_2$—CO),
2.85–3.67 (12H, m, C—4H$_2$, C—6H,

S—CH$_2$—CH$_2$—N, N—CH$_2$—CH$_2$—CO, C—CH$_2$—OH,

OH or NH), 3.93 (2H, m, C—5H, HO—CH—CO), 4.17 (1H, br, NH or OH), 5.17 (1H, d, J = 13.0Hz, CHH—Ar), 5.32 (1H, d, J = 13.0Hz, CHH—Ar), 6.73 (1H, br, NH), 7.35 (5H, s, ArH).

(b) When $CD_2Cl_2+D_2O$ was used as the solvent: δ (ppm):

0.88 (3H, s, CH$_3$—C—), 0.95 (3H, s, CH$_3$—C—)

1.02 (3H, t, J = 7.5H2, CH$_2$=CH$_3$), 1.55–2.00 (2H, m, CH$_2$—CH$_3$), 2.39 (2H, t, J = 6.5Hz, N—CH$_2$—CH$_2$—CO), 2.80–3.67 (11H, m, C—4H$_2$, C—6H,

S—CH$_2$—CH$_2$—N, N—CH$_2$—CH$_2$—CO, C—CH$_2$—OH), 3.93 (1H, dt, J = 3.0Hz, J = 9.0 Hz, C—5H), 3.93 (1H, s, HO—CH—CO—), 5.13 (1H, d, J = 13.0Hz, CHH—Ar), 5.28 (1H, d, J = 13.0 Hz, CHH—Ar), 7.35 (5H, s, ArH).

MS (m/z):

455 (M$^+$—⬡—CH$_3$), 418, 416 (M$^+$—HO—CH(CH$_3$)$_2$—CH$_2$OH—CO), 400 (M$^+$—HO—CH(CH$_3$)$_2$—CH$_2$OH—CONH$_2$), 329, 309 (400-CH$_2$—⬡), 259 (structure with S—CH=CH$_2$, N, COOCH$_2$—⬡).

Cysteamine and $\beta$-alanine were confirmed to be present in the acid hydrolysate (hydrolysis in 6 N hydrochloric acid at 115° C. for 16 hours) of the ester.

From the above physico-chemical properties, the planar structure of antibiotic OA-6129A was determined to be

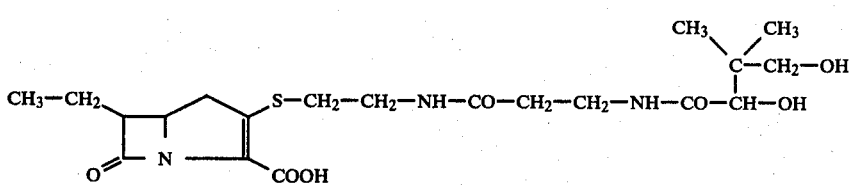

and was considered to have the 5,6-trans configuration.

EXAMPLE 3

Production of p-nitrobenzyl ester of antibiotic OA-6129A:

Antibiotic OA-6129A (63.5 mg) was dissolved in 9.0 ml of dimethyl formamide, and with cooling, 0.2 ml of triethylamine was added. With stirring, 285 mg of p- nitrobenzyl bromide in 1.5 ml of dimethyl formamide was added. The reaction was carried out at the same temperature for 30 minutes, and then for 3 hours at room temperature.

The reaction mixture was poured into 100 ml of ethyl acetate, and the solution was washed with 20 ml of saturated sodium chloride solution in 0.01 M phosphate buffer, pH 8.4. The aqueous layer was separated and extracted with 100 ml of methylene chloride. The organic layer and the methylene chloride extract were combined, dehydrated over anhydrous sodium sulfate, and distilled under reduced pressure.

The residue was dissolved in a small amount of methylene chloride, and applied on a column of 12 g of silica gel. The column was successively developed with benzene/acetone (1/1), benzene/acetone (1/3) and acetone. Under monitoring by silica gel thin layer chromatography (benzene/acetone=1/1), those acetone fractions which showed an ultraviolet absorptive spot at Rf 0.33 were collected and concentrated to dryness under reduced pressure. The yield of the title compound was 36.3 mg.

The resulting p-nitrobenzyl ester of antibiotic OA-6129A showed the following physico-chemical properties.

(1) Specific rotation $[\alpha]_D^{24}$: 37.5° (c=1.0, $CH_2Cl_2$).

(2) Ultraviolet absorption spectrum: $\lambda_{max}^{CH2Cl2}$ nm ($\epsilon$): 319 (8400), 270 (10500).

(3) Main peaks in the infrared absorption spectrum: $\nu_{max}^{CH2Cl2}$ cm$^{-1}$: 1770 ($\beta$-lactam), 1700 (ester), 1665 (amide).

(4) Nuclear magnetic resonance spectrum (solvent $CD_2Cl_2$; internal standard TMS) $\delta$ (ppm):

0.87 (3H, s, CH₃—C—), 0.95 (3H, s, CH₃—C—) [each with CH₃ substituent]

1.04 (3H, t, J = 7.5Hz, CH₂—CH₃), 1.5-2.2 (3H, m, CH₂—CH₃, OH), 2.40 (2H, t, J = 6.5Hz, N—CH₂—CH₂—CO), 2.8-3.7 (12H, m, C—4H₂, C—6H, S—CH₂—CH₂—N,

N—CH₂—CH₂—CO, C—CH₂—OH, OH or NH),

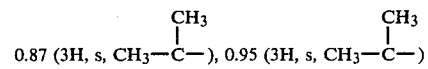

5.19 (1H, d, J = 14Hz, CH.H—Ar), 5.45 (1H, d, J = 14Hz, CH.H—Ar), 6.74 (1H, br, NH), 7.63 (2H, d, J = 9Hz, ArH), 8.18 (2H, d, J = 9Hz, ArH).

EXAMPLE 4

Production of p-nitrobenzyl ester of antibiotic OS-6129B₂:

Sodium salt of antibiotic OA-6129B₂ (190 mg) was dissolved in 6.0 ml of dimethyl formamide. With ice cooling, the solution was mixed with 0.2 ml of triethylamine, and then with 210 mg of p-nitrobenzyl bromide in dimethyl formamide under agitation. The reaction was performed at the same temperature for 5 minutes, and then for 3 hours at room temperature. The reaction mixture was poured into 100 ml of methylene chloride, and washed twice with 20 ml each of a 0.1 M phosphate buffer, pH 6.8. The aqueous layer was separated from the organic layer and extracted twice with 100 ml each of methylene chloride. The methylene chloride and the said organic layer were combined, dehydrated over anhydrous sodium sulfate, and distilled under reduced pressure. The residue was dissolved in a small amount of methylene chloride, and adsorbed on a column of 6 g silica gel. The column was successively developed with benzene/acetone (1/1), benzene/acetone (1/2), benzene/acetone (1/3), benzene/acetone (1/5), and acetone. Active fractions which showed an ultraviolet absorptive spot at Rf 0.15 by thin layer chromatography using benzene/acetone (1/4) were collected from the benzene/acetone (1/5) and acetone eluates, combined and concentrated to dryness to give 85 mg of the title compound.

The compound had the following properties.

(1) Specific rotation $[\alpha]_D^{24}$: 41.4° (c=1.0, dioxane).

(2) Main peaks in the infrared absorption spectrum: $\nu_{max}^{KBr}$ cm$^{-1}$: 1760 ($\beta$-lactam), 1695 (ester), 1640 (amide).

(3) Ultraviolet absorption spectrum: $\nu_{max}^{CH2Cl2}$ nm ($\epsilon$): 320 (10500), 271 (10500).

(4) Nuclear magnetic resonance spectrum (pyridine-d₅) ppm (only those signals which were located in the field of 1 to 5 ppm are shown):

1.30 (6H, s, CH₃—C—CH₃), 1.55 (3H, d, J = 7.0Hz, CH₃—CH), 2.70 (2H, t, J = 6.5Hz, NH—CH₂—CH₂—CO), 2.90-4.05 (11H, m, C—4H₂, C—6H,

S—CH₂—CH₂—NH, NH—CH₂—CH₂—CO, O—CH₂—C—)

4.10-4.50 (2H, m, C—5H, C—8H), 4.52 (1H, s, HO—CH—CO).

(5) Mass spectrum (FD)

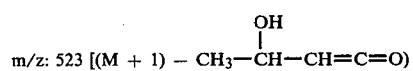

EXAMPLE 5

Production of p-nitrobenzyl ester of triacetyl antibiotic OA-6129B₂:

The p-nitrobenzyl ester of antibiotic OA-6129B₂ (12 mg) was dissolved in 0.5 ml of pyridine, and with stirring under ice cooling, 0.15 ml of acetic anhydride was added. The acetylation was carried out for 5 minutes at the same temperature and then for 3 hours at room temperature. Ice water was added to the reaction mixture, and the mixture was stirred for 10 minutes. The mixture was poured into 20 ml of ethyl acetate, and washed with 10 ml of 0.1 M phosphate buffer, pH 6.8, 10 ml of 0.1 M phosphate buffer, pH 8.4, and the said phosphate buffer, pH 6.8, respectively. The organic phase was dehydrated over anhydrous sodium sulfate, and then distilled under reduced pressure. The residue was dissolved in a small amount of methylene chloride, and adsorbed on a column of 2 g silica gel. The column was developed successively with benzene/acetone mixtures at mixing ratios of 5:1, 3:1, 1:1, 2:1, and 1:5. Active fractions obtained from the benzene/acetone (1/1) eluate were combined and concentrated to give 7.9 mg of the title compound which showed an ultraviolet absorptive spot at Rf 0.59 by silica gel thin-layer chromatography using benzene/acetone (1/3) as a developing solvent.

The product showed the following properties.
(1) Specific rotation $[\alpha]_D^{24}$: 23.2° (c=0.5, $CHCl_3$).
(2) Main peaks in the infrared absorption spectrum:

$\nu_{max}^{CHCl_3}$ cm$^{-1}$: 1780 ($\beta$-lactam), 1735 (ester), 1672 (amide).

(3) Ultraviolet absorption spectrum: $\lambda_{max}^{CHCl_3}$ nm ($\epsilon$): 320 (12000), 270 (12000).

(4) Nuclear magnetic resonance spectrum ($CDCl_3$): $\delta$ ppm:

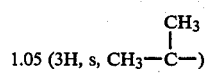
1.05 (3H, s, $CH_3-C-$)

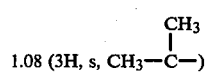
1.08 (3H, s, $CH_3-C-$)

1.43 (3H, d, J = 7.0Hz, $CH_3-CH$), 2.03 (3H, s, $CH_3CO$), 2.10 (3H, s, $CH_3CO$), 2.13 (3H, s, $CH_3CO$), 2.38 (2H, t, J = 6.0Hz, $NH-CH_2-CH_2-CO$), 2.70–3.70 (9H, m, C—4$H_2$, C—6H,

S—$CH_2$—$CH_2$—NH, NH—$CH_2$—$CH_2$—CO), 3.82 (1H, d, J = 11.5Hz, CHH—OAc), 4.02 (1H, d, J = 11.5Hz, CHH—OAc), 3.97–4.27 (1H, m, C—5H), 4.80 (1H, s, CH—OAc), 5.10–5.45 (1H, m, C—8H), 5.22 (1H, d, J = 14.5Hz, CHH—Ar), 5.50 (1H, d, J = 14.5Hz, CHH— Ar), 6.29 (1H, br. NH), 6.75 (1H, br, NH), 7.63 (2H, d, J = 9.0Hz, Ar.H), 8.21 (2H, d, J = 9.0Hz, Ar.H).

(4) Mass spectrum (FD): m/z: 735 (M+1).

From the foregoing physico-chemical properties, the planar structure of the antibiotic OA-6129B$_2$ was determined to be

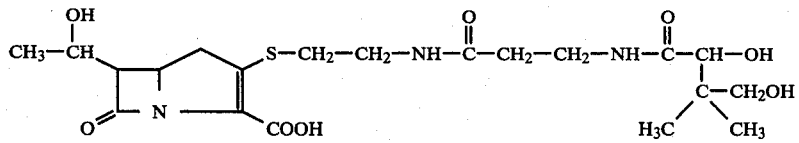

with the 5,6-trans configuration.

What we claim is:
1. A compound of the formula

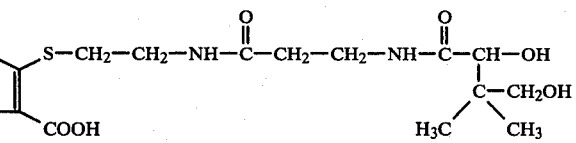

wherein $R_1$ represents a hydrogen atom, —OH or —OSO$_3$H, and $R_2$ represents a hydrogen atom, benzyl or benzyl substituted by 1 to 3 substituents selected from lower alkyl, lower alkoxy, halogen and nitro; or a pharmaceutically acceptable salt thereof.

2. A compound of claim 1 in which $R_1$ is a hydrogen atom and the 5,6 configuration is trans.

3. A compound of claim 1 in which $R_1$ is —OH, and the 5,6 configuration is cis or trans.

4. A compound of claim 1 in which $R_1$ is —OSO$_3$H, and the 5,6 configuration is cis.

5. A compound of claim 1 in which $R_2$ is a hydrogen atom, benzyl or p-nitrobenzyl.

6. A compound of claim 1 wherein the salt is a sodium salt.

7. An antimicrobial composition which comprises an antimicrobially effective amount of a compound of the formula

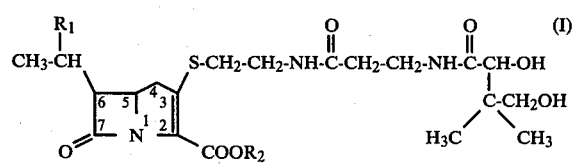

wherein $R_1$ represents a hydrogen atom, —OH, or —OSO$_3$H, or a pharmaceutically acceptable salt thereof, and a pharmaceutically acceptable carrier or diluent.

* * * * *